(12) United States Patent
Hsieh

(10) Patent No.: US 6,421,552 B1
(45) Date of Patent: Jul. 16, 2002

(54) METHODS AND APPARATUS FOR ESTIMATING CARDIAC MOTION USING PROJECTION DATA

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/472,560

(22) Filed: Dec. 27, 1999

(51) Int. Cl.[7] .................................................. A61B 5/05
(52) U.S. Cl. ........................ 600/425; 600/427; 600/428; 378/4; 378/8; 378/69; 378/95; 378/115; 250/363.04; 382/131
(58) Field of Search ................................. 600/425, 413, 600/414, 427, 428; 378/4, 8, 69, 95, 115; 250/363.04; 382/131

(56) References Cited

U.S. PATENT DOCUMENTS

| | | | |
|---|---|---|---|
| 3,952,201 A | | 4/1976 | Hounsfield |
| 4,182,311 A | * | 1/1980 | Seppi et al. |
| 4,382,184 A | * | 5/1983 | Wernikoff |
| 4,530,109 A | | 7/1985 | Klausz |
| 4,641,328 A | | 2/1987 | Fujise |
| 4,837,686 A | | 6/1989 | Sones et al. |
| 4,994,965 A | * | 2/1991 | Crawford et al. |
| 5,490,516 A | * | 2/1996 | Hutson |
| 5,533,085 A | | 7/1996 | Sheehan et al. |
| 5,544,212 A | | 8/1996 | Heuscher |
| 5,602,891 A | * | 2/1997 | Pearlman |
| 5,647,360 A | * | 7/1997 | Bani-Hashemi et al. |
| 5,682,887 A | * | 11/1997 | Xu et al. |
| 5,751,782 A | | 5/1998 | Yoshitome |
| 5,832,051 A | | 11/1998 | Lutz |
| 6,041,097 A | * | 3/2000 | Roos et al. |
| 6,154,516 A | * | 11/2000 | Heuscher et al. |
| 6,185,271 B1 | * | 2/2001 | Kinsinger |

FOREIGN PATENT DOCUMENTS

| | | |
|---|---|---|
| EP | 0 370 341 A2 | 5/1990 |
| EP | 1 013 225 A1 | 6/2000 |
| EP | 1 016 376 A2 | 7/2000 |
| EP | 1 050 272 A1 | 11/2000 |
| EP | 1 072 224 A2 | 1/2001 |
| EP | 1 088 517 A1 | 4/2001 |
| EP | 1 090 586 A2 | 4/2001 |
| EP | 1 092 392 A2 | 4/2001 |
| WO | WO 00/30539 | 6/2000 |
| WO | WO 00/33252 | 6/2000 |

OTHER PUBLICATIONS

Broderick et al., "Measurement of Coronary Artery Calcium with Dual–Slice Helical CT Compared with Coronary Angiography: Evaluation of CT Scoring Methods, Interobserver Variations, and Reproducibility," AJR:167, Aug., 1996, pp. 439–444.

Yoon et al., "Coronary Artery Calcium: Alternate Methods for Accurate and Reproducible Quantitation," Acad Radiol 1997; 4:666–673.

(List continued on next page.)

*Primary Examiner*—Marvin M. Lateef
*Assistant Examiner*—Jeoyuh Lin
(74) *Attorney, Agent, or Firm*—Carl B. Horton, Esq.; Armstrong Teasdale LLP

(57) ABSTRACT

A method for estimating motion of a part of an object, using a CT imaging system, is therefore provided in one embodiment of the present invention. This method includes steps of: scanning the object with the CT imaging system so as to acquire conjugate data samples; analyzing the conjugate data samples to remove data representative of overlapping, non-moving portions of the object; and estimating a cardiac motion from the analyzed conjugate data samples.

Advantageously, no EKG device is required estimating cardiac motion when this method for estimating motion is employed.

29 Claims, 3 Drawing Sheets

OTHER PUBLICATIONS

Agatston et al., "Quantification of Coronary Artery Calcium Using Ultrafast Computed Tomography," JACC vol. 15, No. 4, Mar. 15, 1990, pp. 827–832.

Ukai et al., "A Coronary Calcification Diagnosis System Based on Helical CT Images," 1998 IEEE, pp. 1208–1212.

Wilson et al., "Automated Detection of Mirocalcifications in Mammograms through Application of Image Pixel Remapping and Statistical Filter," Eleventh IEEE Symposium on Computer–Based Medical Systems, 1998, pp. 270–274.

Ohhashi et al., "Application of a Neural Network to Automatic Gray–level Adjustment for Medical Images," 1991 IEEE International Joint Conference on Neural Networks, vol. 2, pp. 974–980, Nov. 18–21, 1991, Singapore.

Woodhouse et al., "Coronary Arteries: Retrospective Cardiac Gating Technique to Reduce Cardiac Motion Artifact at Spiral CT," Radiology, Aug. 1997, pp. 566–569.

Spraggins et al., "Retrospective Cardiac Gating Requiring No Physiological Monitoring," undated, one page.

* cited by examiner

METHODS AND APPARATUS FOR ESTIMATING CARDIAC MOTION USING PROJECTION DATA

BACKGROUND OF THE INVENTION

This invention relates generally to methods and apparatus for computed tomography (CT) imaging of moving objects, and more particularly to methods and apparatus for CT imaging of a patient's heart.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Application of conventional computed tomography (CT) to cardiac applications has gained significant interests recently, as a result of the success of the calcification scoring and the development of phrase coded cardiac reconstruction. In both developments, the use of EKG signals is an integral part of the process, where the patient and the scanner have to be connected to an EKG monitoring device. The disadvantages of such an approach are multiple. First, the EKG device provides extra cost to the examination. Second, the attachment and detachment of EKG leads are time consuming and cumbersome. Third, it is well known that the electric signal provided by the EKG does not exactly match the mechanical motion of the heart, due to variations in the delay from patient to patient.

Therefore, it would be desirable to provide methods and apparatus to estimate cardiac motion using acquired CT projection data, but without requiring use of an EKG device.

BRIEF SUMMARY OF THE INVENTION

A method for estimating motion of a part of an object, using a CT imaging system, is therefore provided in one embodiment of the present invention. This method includes steps of: scanning the object with the CT imaging system so as to acquire conjugate data samples; analyzing the conjugate data samples to remove data representative of overlapping, non-moving portions of the object; and estimating a cardiac motion from the analyzed conjugate data samples.

When the method described above is used to estimate cardiac motion, no EKG device is required for such estimation.

DETAILED DESCRIPTION OF THE INVENTION

Figure 1:
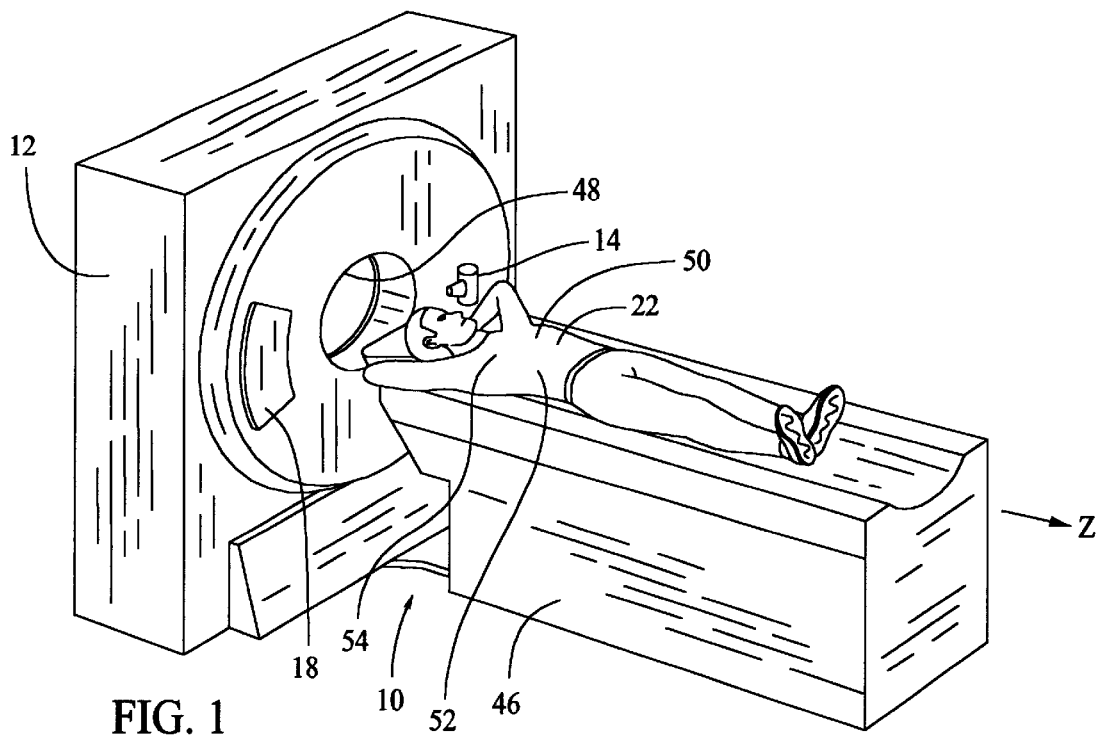
FIG. 1 is a pictorial view of a CT imaging system.
Figure 2:
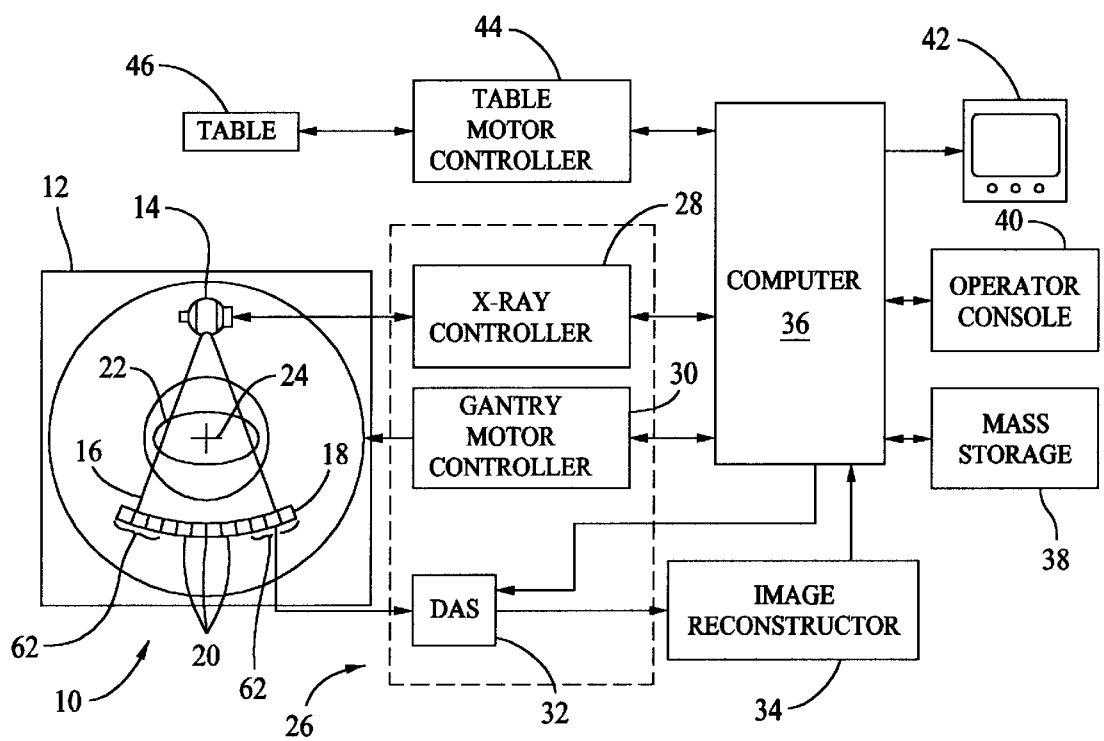
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The present invention advantageously uses the fact that, in cardiac scanning, the main source of object motion is the heart 50 of patient 22, particularly in axial scan mode with patient breath-holding. Therefore, object or patient 22 is scanned by imaging system 10, to collect data samples, including conjugate data samples that differ by either π or 2π in projection angle. The conjugate projection samples are analyzed to remove all overlapped structures (such as ribs 52 and chest walls 54 of patient 22), and an image of object or patient 22 is reconstructed from the analyzed samples. In one embodiment, conjugate data samples are differenced. The remaining data samples represent a difference signal resulting from cardiac motion, and are used to estimate cardiac motion.

Figure 3:
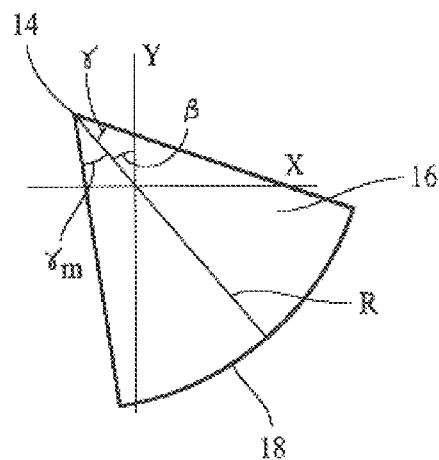
FIG. 3 is a geometrical representation of the radiation source and detector of the CT imaging system illustrated in FIG. 1, showing projection angle $\beta$, detector angle $\gamma$, and maximum detector angle $\gamma_m$.

Utilizing a fan beam of radiation 16, conjugate rays of a projection that differ by π are acquired in an extended period of time. For example, and referring to FIG. 3, radiation source 14 projects a radiation beam 16 at detector 18, where the x- and y-axes are perpendicular to an axis of rotation of gantry 12. In FIG. 3, $\beta$ represents a projection angle, $\gamma$ represents a detector angle, and $\gamma_m$ is a maximum detector angle. Detector angle $\gamma$ is an angle formed by any ray in a projection with the isoray R of the same projection.) a conjugate ray to $(\gamma,\beta)$ is $(-\gamma, \beta+\pi-2\gamma)$. For $-\gamma_m<\gamma<\gamma_m$, a corresponding $\beta$ varies in a range of $(\beta+\pi-2\gamma_m, \beta+\pi+2\gamma_m)$, which covers a projection angle range of $4\gamma_m$, corresponding to roughly ⅛ of a rotation. Therefore, for an embodiment utilizing a 1.0 s scan speed, conjugate rays are collected over 0.125 s time interval. During this period, significant cardiac motion of heart 50 is encountered. Significant cardiac motion is also encountered during collection of conjugate samples along a line $\beta=\gamma_m-\gamma$. In another embodiment, a faster scan speed is used. For example, utilizing a 0.5 s scan speed, conjugate samples are collected over a 62.5 ms interval, which is a small portion of the cardiac cycle.

In one embodiment utilizing a 1.0 s scan speed, conjugate samples that are 2π apart are utilized. In this embodiment, a conjugate sample set corresponding to a single projection is another projection. Therefore, both sample sets are collected in a very short period of time. Within each projection, the cardiac motion is small enough to be ignored.

Figure 4:
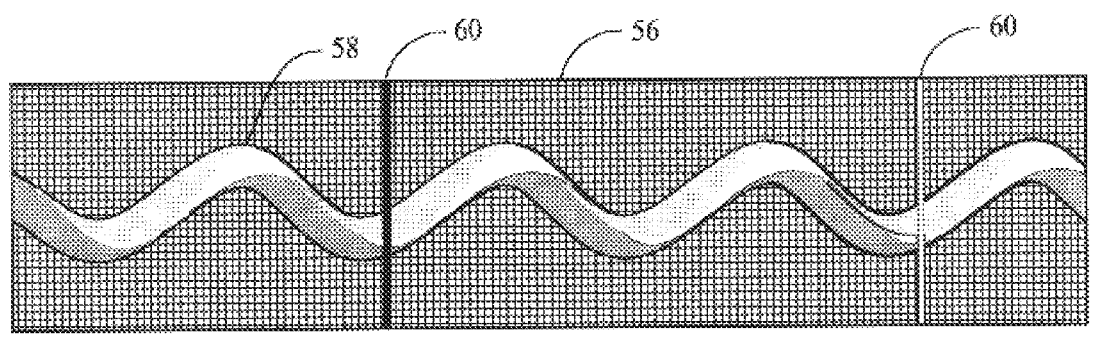
FIG. 4 is an image representing differential projection data corresponding to four gantry rotations (after pre-processing and calibration) obtained in an animal experiment.

Referring to FIG. 4, an image 56 representing differential projection data corresponding to four gantry rotations (after pre-processing and calibration) obtained in an animal experiment is shown. View varies along the horizontal axis; detector element 20 position (corresponding to different DAS channels) varies along the vertical axis. In this study, a pig was scanned at 1.0 s scan speed and EKG signals were recorded. The heart rate of the pig was roughly 100 beats per minute, significantly higher than typical human heart rates. Image 56 clearly shows a sinogram 58 of the pig's heart with all other overlapping structures removed. Since projections that are 2π apart are acquired at different instants in time, results are sensitive to errors due to variation in photon flux, data collection accuracy, and imperfect calibration. Errors are observed as vertical streaks 60 in the image.

To guard against these errors, additional processing was applied to the differential signal. In general, a heart is located near a center region of the view and away from edge cells, i.e., detector elements 62 located at extremities of detector 18 (as shown in FIG. 2). It is relatively simple to position a patient 22 on table 46 so that the heart of patient 22 is within the center 45 cm field of view, away from these edge cells. Therefore, edge cells from both sides of detector 18 should contain no cardiac motion influence.

Figure 5:
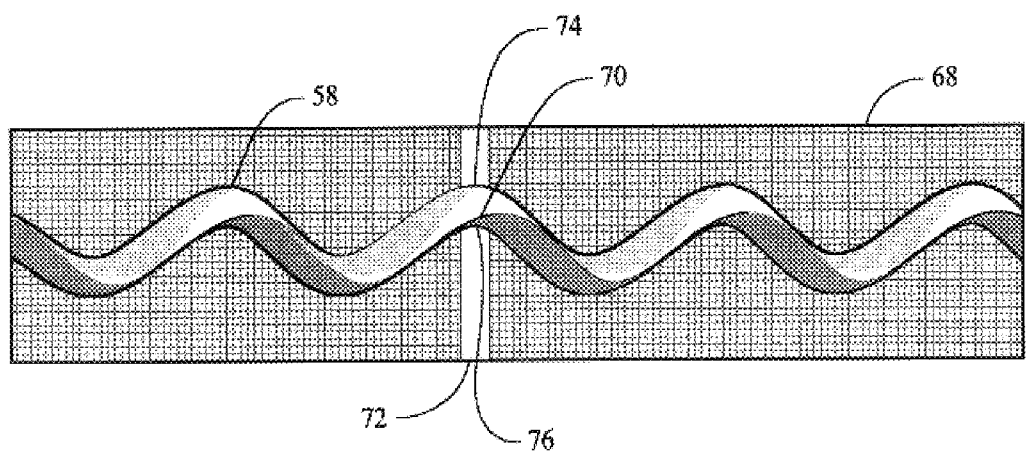
FIG. 5 depicts the differential projections of FIG. 4 processed with an embodiment of the present invention employing a bias correction.

In one embodiment and referring to FIG. 5, the average of these edge cells was used to determine a bias induced by differential signal estimation. FIG. 5 depicts the differential projections of FIG. 4 processed with an embodiment employing a bias correction. The bias correction employed in this embodiment utilized an average of 21 channels from both sides of detector array 18 to determine a DC bias on a view-to-view basis. The DC bias was then subtracted from the differential data signals one view at a time. As a result, vertical streaks 60 appearing in FIG. 4 were nearly eliminated.

In other embodiments, other methods for bias compensation are used. For example, in one embodiment, a scaling factor is determined in a manner similar to that in which the DC bias is determined and is used to multiply each projection. An average $S_{AV}$ of 21 edge detector channels $S_i$ is determined over all views. For each projection view i, the average $S_i$ of the 21 edge channels is determined and the scaling factor for the view is $S_{AV}/S_i$.

Figure 6:
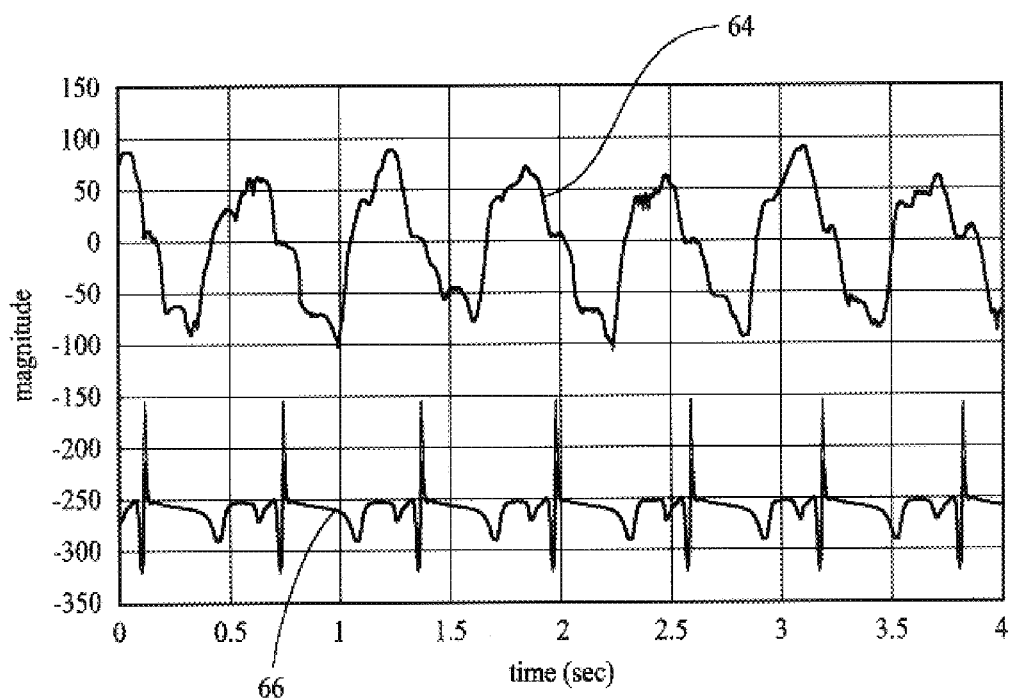
FIG. 6 is a comparison of a cardiac motion signature determined by one embodiment of the present invention and a corresponding EKG signal.

In one embodiment, after a differential image is reconstructed, a cardiac motion signature is determined. For example, an average differential data signal for each view is used as an indicator for an amount of cardiac motion. FIG. 6 shows a comparison between a determined cardiac motion signature 64 and a corresponding EKG signal 66. Cardiac motion signature 64 estimation is based on CT projection data. FIG. 6 shows that a very accurate and consistent correspondence is achieved between signature 64 and EKG signal 66, demonstrating that projection estimation provides a suitable alternative to EKG signal 66.

In the generation of FIG. 6, only an average signal for each view was used as a motion indicator. In another embodiment, other motion indicators are used. For example, maximum and minimum variations within each view are used to indicate cardiac motion.

In one embodiment, a reconstructed differential image 68 such as that of FIG. 5 is used to automatically identify a location of heart 50 of patient 22 either in projection space or in image space. Thresholds are applied to the acquired data to isolate heart 50 in the projection. As can be seen in FIG. 5, the only region 70 registering significant readings is heart 50. By defining the heart region 70 at view 72 in which an intensity of differential image 68 is larger than a predefined threshold, left and right edges 74 and 76 respectively of heart 50 are isolated on the projection. By incorporating heart projection boundaries 74, 76 from view to view, inaccuracies in heart 50 boundary estimation are further reduced. To further reduce inaccuracies, regions in the differential image within the heart boundary are multiplied by a weighting function prior to the average signal calculation. The weighting function provides less weight to the regions near the edge of the heart and higher weight well inside the heart. After boundaries 74, 76 are identified on projection 68, a corresponding heart region 70 in the image is identified and used for other cardiac image analysis, such as ejection fraction, contrast analysis, etc. In one embodiment, boundary identification is used to refine the cardiac signature derivation by focusing only in heart region 70, completely removing the influence of non-heart objects.

After a cardiac signal is obtained, in one embodiment, the impact of noise on images is further reduced. Such reduction is achieved, for example, by low-pass filtering or curve fitting. Curve fitting to obtain a signature curve advantageously makes it easier to identify phases and periodicity of the heart utilizing the fitted curves and fitting parameters.

In one embodiment, CT imaging system 10 scans a patient 22 on table 46 by rotating gantry 12 while x-ray source 14 is energized. Signals from detector array 18 are processed by DAS 32 and image reconstructor 34. Computer 36 is programmed to perform data processing steps of one or more method embodiments described above, and resulting images and/or data (for example, a cardiac motion signature) is displayed on display 42.

From the preceding description of various embodiments of the present invention, it is evident that cardiac motion is accurately estimated from acquired CT projection data. Furthermore, the methods and apparatus of this invention advantageously provide such estimation without requiring the use of an EKG device.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan, however, the invention may be used with a helical scan although more than 360° of data are required. Accordingly, the spirit and scope of the invention are to be limited only by the terms of the appended claims and legal equivalents.

What is claimed is:

1. A method for estimating motion of a part of an object, using a CT imaging system, said method comprising the steps of:
    scanning the object with the CT imaging system so as to acquire conjugate data samples;
    analyzing the conjugate data samples to remove data representative of overlapping, non-moving portions of the object; and
    estimating a cardiac motion from the analyzed conjugate data samples.

2. A method in accordance with claim 1 wherein analyzing the conjugate data samples comprises the step of differencing the conjugate data samples.

3. A method in accordance with claim 1 wherein analyzing the conjugate data samples comprises the steps of deriving a scaling factor to multiply each projection.

4. A method in accordance with claim 1 wherein the object is a patient, and the step of analyzing the conjugate samples to remove overlapping, non-moving portions of the object comprises removing data representative of the patient's ribs and chest walls.

5. A method in accordance with claim 4 further comprising the step of applying a threshold to the analyzed data to identify heart edges represented in the analyzed data.

6. A method in accordance with claim 5 further comprising the steps of reconstructing an image from the analyzed data and identifying heart projection boundaries from view to view to identify a heart region in the image.

7. A method in accordance with claim 6 further comprising the step of reducing image noise by at least one of low pass filtering and curve fitting the analyzed data used to produce the reconstructed image.

8. A method in accordance with claim 6 further comprising the step of determining a cardiac motion signature.

9. A method in accordance with claim 8 wherein analyzing the conjugate data samples comprises the step of differencing the conjugate data samples;
    and wherein determining a cardiac motion signature comprises the step of averaging the differenced conjugate data samples for each view to indicate an amount of cardiac motion.

10. A method in accordance with claim 5 and further comprising the step of scoring the image of the patient's heart for calcification.

11. A method in accordance with claim 5 further comprising the step of positioning the patient so that the patient's heart is within a center 45 cm field of view.

12. A method in accordance with claim 1 wherein analyzing the conjugate data samples comprises the step of differencing conjugate data samples differing in projection angle by an integral multiple of $\pi$.

13. A method in accordance with claim 1 wherein the conjugate data samples are acquired over a time interval of between 0 sec and $\frac{1}{8}$ sec.

14. A method in accordance with claim 1 wherein the acquired conjugate data samples include data samples representative of edge cells; and wherein
    analyzing the conjugate data samples to remove data representative of overlapping, non-moving portions of the object comprises the steps of differencing the conjugate data samples and averaging data samples representative of edge cells to determine a bias induced in the differenced conjugate data samples.

15. A method in accordance with claim 14 wherein the CT imaging system comprises a detector array having a plurality of detector elements;
    averaging data representative of edge cells comprises the step of averaging data acquired from detector elements located at opposite ends of the detector array to determine a view-to-view DC bias;
    and said method further comprises the step of subtracting the DC bias from the differential signals one view at a time.

16. A CT imaging system for estimating motion of a part of an object, said CT imaging system comprising a computer, said computer configured to:
    scan the object so as to acquire conjugate data samples;
    analyze the conjugate data samples to remove data representative of overlapping, non-moving portions of the object; and
    estimate a cardiac motion from the analyzed conjugate data samples.

17. A CT imaging system in accordance with claim 16 wherein said system being configured to analyze the conjugate data samples comprises said system being configured to difference the conjugate data samples.

18. A CT imaging system in accordance with claim 16 wherein said system being configured to analyze the conjugate data samples comprises said system being configured to derive a scaling factor to multiply each projection.

19. A CT imaging system in accordance with claim 16 wherein the object is a patient, and said system being configured to analyze the conjugate samples to remove overlapping, non-moving portions of the object comprises said system being configured to remove data representative of the patient's ribs and chest walls.

20. A CT imaging system in accordance with claim 19 further configured to apply a threshold to the analyzed data to identify heart edges represented in the analyzed data.

21. A CT imaging system in accordance with claim 20 further configured to reconstruct an image from the analyzed data and to identify heart projection boundaries from view to view to identify a heart region in the image.

22. A CT imaging system in accordance with claim 21 further configured to reduce image noise by at least one of low pass filtering and curve fitting the analyzed data used to produce the reconstructed image.

23. A CT imaging system in accordance with claim 21 further configured to determine a cardiac motion signature.

24. A CT imaging system in accordance with claim 23 wherein said system being configured to analyze the conjugate data samples comprises said system being configured to difference the conjugate data samples; and wherein said system being configured to determine a cardiac motion signature comprises said system being configured to average the differenced conjugate data samples for each view to indicate an amount of cardiac motion.

25. A CT imaging system in accordance with claim 20 further configured to support the patient so that the patient's heart is within a center 45 cm field of view.

26. A CT imaging system in accordance with claim 16 wherein said system being configured to analyze the conjugate data samples comprises said system being configured to difference conjugate data samples differing in projection angle by an integral multiple of $\pi$.

27. A CT imaging system in accordance with claim 16 configured to acquire the conjugate data samples over a time interval of between 0 sec and $\frac{1}{8}$ sec.

28. A CT imaging system in accordance with claim 16 configured to acquire conjugate data samples including data samples representative of edge cells; and wherein said system being configured to analyze the conjugate data samples to remove data representative of overlapping, non-moving portions of the object comprises said system being configured to difference the conjugate data samples and to average data samples representative of edge cells to determine a bias induced in the differenced conjugate data samples.

29. A CT imaging system in accordance with claim 28 further comprising a detector array having a plurality of detector elements;

wherein said system being configured to average data representative of edge cells comprises said system being configured to average data acquired from detector elements located at opposite ends of the detector array to determine a view-to-view DC bias;

and said system is further configured to subtract the DC bias from the differential signals one view at a time.

* * * * *